United States Patent [19]
Barton et al.

[11] Patent Number: 4,490,296
[45] Date of Patent: Dec. 25, 1984

[54] COMPOSITIONS AND METHOD

[75] Inventors: Derek H. R. Barton; William B. Motherwell; Samir Z. Zard, all of Gif-Sur-Yvette, France

[73] Assignee: Roussel Uclaf, Paris, France

[21] Appl. No.: 462,684

[22] Filed: Jan. 31, 1983

[30] Foreign Application Priority Data

Feb. 18, 1982 [FR] France ................................ 82 02681

[51] Int. Cl.$^3$ ............................................... C07J 5/00
[52] U.S. Cl. .............................. 260/397.4; 260/397.5; 502/167
[58] Field of Search ........................ 260/397.5, 397.4; 252/438

[56] References Cited

U.S. PATENT DOCUMENTS 3,980,681  9/1976  Sykes et al. ...................... 260/397.5

Primary Examiner—Elbert L. Roberts
Attorney, Agent, or Firm—Charles A. Muserlian

[57] ABSTRACT

A novel nitromethylation composition comprising nitromethane and a catalytic amount of a bifunctional basic catalyst, optionally in an organic solvent, a method of nitromethylating ketonic compounds with said compositions and novel steroids of the formulae

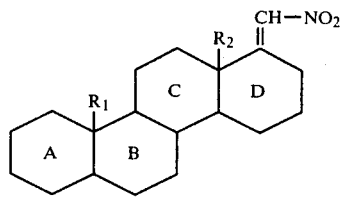

and

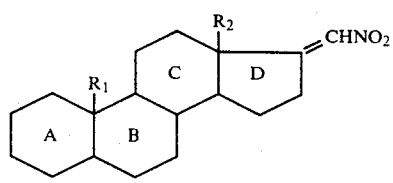

wherein $R_1$ is selected from the group consisting of hydrogen, alkyl of 1 to 4 carbon atoms optionally substituted with an oxygen or nitrogen group or halogen and alkenyl and alkynyl of 2 to 4 carbon atoms, $R_2$ is alkyl of 1 to 4 carbon atoms and the A,B,C and D rings optionally contain at least one double bond and optionally substituted with at least one member of the group consisting of —OH, =O, halogen, alkyl and alkoxy of 1 to 4 carbon atoms and alkenyl and alkynyl of 2 to 4 carbon atoms and their use to form the corresponding 21-acetoxy-20-ketocorticosteroids compounds in a simple manner.

17 Claims, No Drawings

COMPOSITIONS AND METHOD

STATE OF THE ART

Various methods of nitromethylating ketones are described in the literature. Wey et al [J. Chem. Soc., 1957, p. 2926] describe reacting 3-benzoyl-4-methoxy-benzaldehyde with nitromethane in the presence of methylamine hydrochloride in ethanol. Barton et al [J. Chem. Soc., 1965, p. 6387] describe reacting 3,4-dibenzoyl-benzaldehyde with nitromethane and methylamine hydrochloride in sodium acetate presence. Ramirez et al [J.A.C.S., Vol. 72 (1950), p. 2781] describe reacting 3-methoxy-4-hydroxy-benzaldehyde with nitromethane and methylamine hydrochloride in methanol and Cocker [J.Chem. Soc., 1965, p. 1035] describes the reaction of 2-benzyloxy-4-methoxy-benzaldehyde with nitromethane in the presence of methylamine hydrochloride in ethanol. None of these effects the nitromethylation in the presence of a difunctional basis catalyst.

OBJECTS OF THE INVENTION

It is an object of the invention to provide a novel nitromethylation composition and to a novel method of nitromethylating ketones.

It is another object of the invention to provide the novel steroids of formulae I and I'.

It is a further object of the invention to provide a novel process for reacting the compounds of formulae I and I' to obtain the corresponding 21-acetoxy-20-keto-corticosteroids and novel intermediates therefor.

These and other objects and advantages of the invention will become obvious from the following detailed description.

THE INVENTION

The novel nitromethylating compositions of the invention are comprised of nitromethane and a catalytic amount of a bifunctional basis catalyst, optionally in an organic solvent. In the case of nitromethane also serves as solvent, therefore, the amount of catalyst may vary from 0.05 to 20% by volume and preferably 0.5 to 8% based on the volume of nitromethane. When a solvent other than nitromethane is used, the amount of catalyst may vary from 0.1 to 5% by volume. It is preferred that nitromethane is also used as solvent.

Examples of suitable bifunctional basic catalysts are diamines such as ethylene diamine, trimethylenediamine and tetramethylenediamine as well as other bifunctional bases.

In the process of the invention for nitromethylation of an organic cyclic or acyclic ketone to form the corresponding nitromethylene compound, the improvement comprises using as the nitromethylating agent a composition containing nitromethane and a catalytic amount of a bifunctional basic catalyst. The reaction may be illustrated as follows

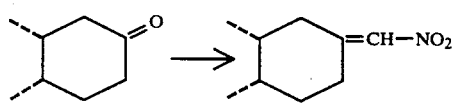

A preferred mode of the process of the invention comprises reacting a ketone of the formula

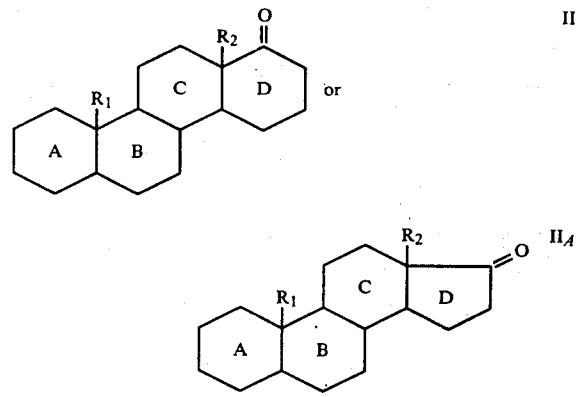

wherein $R_1$ is selected from the group consisting of hydrogen, alkyl of 1 to 4 carbon atoms optionally substituted with an oxygen or nitrogen group or halogen and alkenyl and alkynyl of 2 to 4 carbon atoms, $R_2$ is alkyl of 1 to 4 carbon atoms and the A,B,C and D rings optionally contain at least one double bond and optionally substituted with at least one member of the group consisting of —OH, =O, halogen, alkyl and alkoxy of 1 to 4 carbon atoms and alkenyl and alkynyl of 2 to 4 carbon atoms with nitromethane containing a catalytic amount of a bifunctional basic catalyst to obtain a compound of the formula

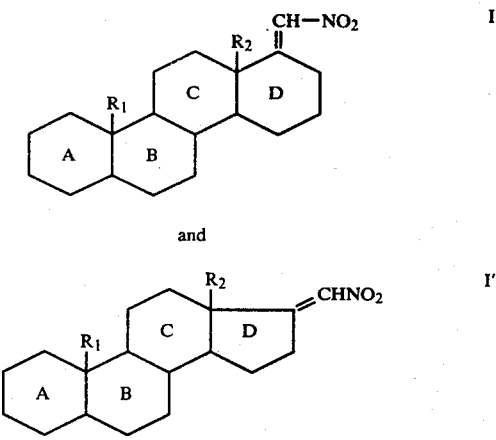

In the said compounds, $R_1$ is preferably selected from the group consisting of alkyl such as methyl or ethyl; alkyl with an oxygen function such as hydroxymethyl, hydroxyethyl, formyl or acetyl; alkyl with a nitrogen function such as cyano, aminomethyl or aminoethyl; alkyl substituted with halogen such as —CH$_2$Hal wherein Hal is a halogen such as chlorine, fluorine or bromine; alkenyl such as vinyl or allyl; and alkynyl such as ethynyl. $R_2$ is preferably methyl or ethyl.

When the A,B,C and D rings contain at least one double bond, the double bonds are preferably 1(2), 3(4), 4(5) or 9(11) or a conjugated double bond system such as 3(4) and 5(6) or 4(5) and 6(7) or 1(2) 4(5) or a three double bond system such as 1(2), 4(5) and 6(7) or an aromatic system with double bonds in the 1,3 and 5-position. When the A,B,C and D rings are substituted with at least one hydroxyl group, they are preferably in the 3- and/or 11-positions. When the said rings are substituted with at least one ketone group, they are preferably in the 3- and/or 11-positions.

When the A,B,C and D rings are substituted with at least one halogen, they are preferably fluorine, chlorine or bromine in the 6- or 9α-position, for example. When the said rings are substituted with at least one alkyl, they are preferably methyl or ethyl in the 2-, 6-, 7- and 16α- or 16β-positions. When the said rings are substituted with at least one alkoxy group, they are preferably methoxy or ethoxy in the 3- or 11β-positions. When the said rings are substituted with at least one alkenyl or alkynyl group, they are preferably vinyl, allyl or ethynyl in the 11β-position, for example.

In a preferred mode of the invention, the starting compound has the formula

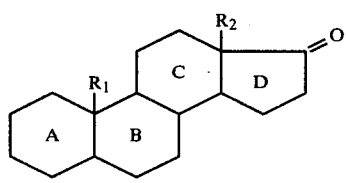   II$_A$ and the final product has the formula I'. Particularly preferred as starting compounds of formula II$_A$ are those where R$_2$ is methyl and those where R$_1$ is methyl or hydrogen.

A more preferred embodiment of the invention comprises reacting a compound of the formula

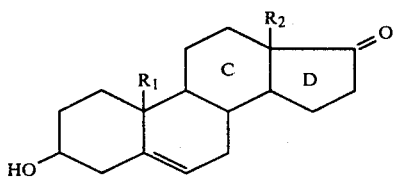   II$_A'$ or more preferably of the formula

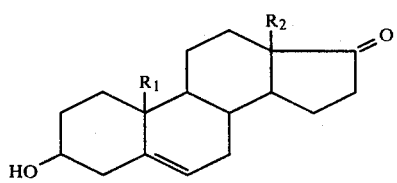   II$_A''$ to nitromethylation to obtain a compound of the formula

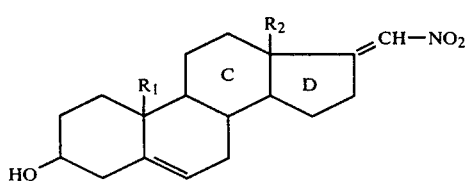   I$_A'$ or more especially a compound of the formula

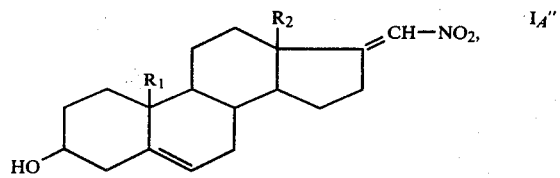   I$_A''$ respectively

A most preferred process of the invention reacts Δ$^5$-androstene-3β-ol-17-one to obtain 17-(nitromethylene)-Δ$^5$-androstene-3β-ol.

The process of the invention is not limited to the treatment of steroidal ketones but is generally applicable to cyclic and acyclic organic compounds.

The compounds of formulae I and I' are novel compounds and the compounds of formula I' and especially those wherein R$_2$ is methyl and those wherein R$_1$ is methyl or hydrogen are preferred. The compounds of formulae I'$_A$ and I''$_A$ are especially preferred, and particularly 17-(nitromethylene)Δ$^5$-androstene-3β-ol.

The compounds of formulae I and I' have a very great industrial interest as they are directly prepared in a simple and economical manner in excellent yields from the corresponding 17-keto steroids and are easily transformed into the corresponding 21-acetoxy-20-keto-corticosteroids with an optional double bond in the 16(17)-position without the necessity of isolating the intermediate products.

The compounds of formula I' are useful to prepare the corresponding 21-acetoxy-20-keto steroids described in French Pat. Nos. 1,058,850 and No. 1,021,728 and U.S. Pat. No. 3,445,490 and German application No. 2,521,231. The compounds of formulae I and I' are useful for preparing steroids known to possess a very great interest as medicaments such as triamcinolone and its derivatives.

The novel process of the invention for the preparation of a 21-acetoxy-20-keto steroid of the formula

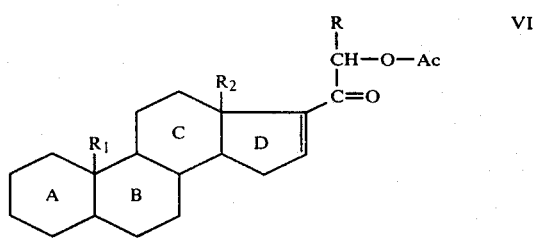   VI wherein A,B,C and D and R$_1$ and R$_2$ have the above definitions and R is selected from the group consisting of hydrogen and alkyl of 1 to 18 carbon atoms comprises reacting a compound of formula I' with aldehyde of the formula RCHO to obtain a compound of the formula

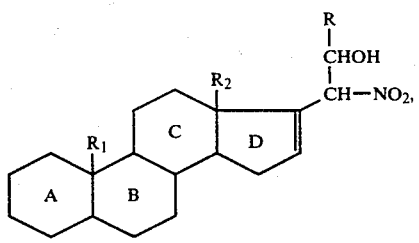

reacting the latter with an esterification of an acid AcOH wherein Ac is acyl of 1 to 18 carbon atoms to obtain a compound of the formula

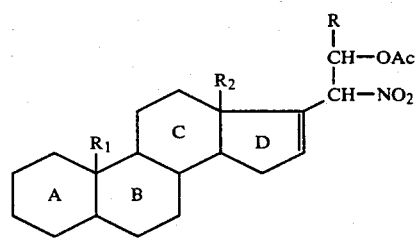

subjecting the latter to a reducing agent for the nitro group to obtain a compound of the formula

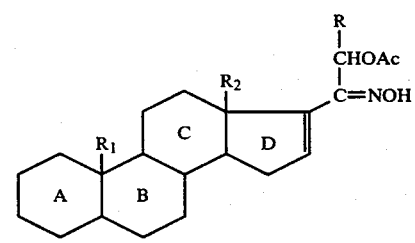

and subjecting the latter to a cleavage agent for the oxime function to obtain a compound of formula VI.

In a preferred mode of the process, the aldehyde is acetaldehyde or formaldehyde and the esterification agent is acetic acid, acetic anhydride, acetyl chloride or any other acid anhydride or acid chloride with or without a catalyst. The preferred reducing agent is chromous chloride or titanium trichloride. The cleavage agent is preferably an aqueous solution of titanium trichloride or acetic acid in the presence of an alkali metal nitrate or an aqueous mineral acid in the presence of an aldehyde.

In a variation of the latter process of the invention, the compound of formula I' is reacted with a reducing agent for the 17(20) double bond to obtain a compound of the formula

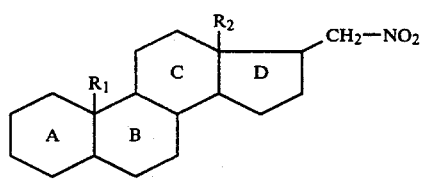

reacting the latter with an aldehyde of the formula RCHO to obtain a compound of the formula

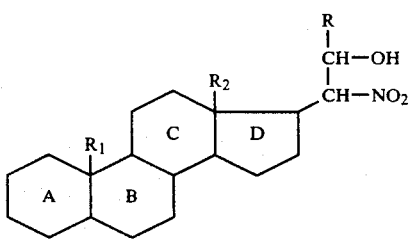

reacting the latter with an esterification agent to obtain the compound of the formula

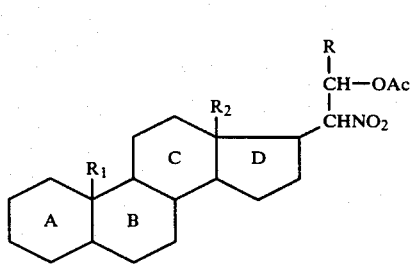

reacting the latter with a reducing agent for the nitro group to obtain a compound of the formula

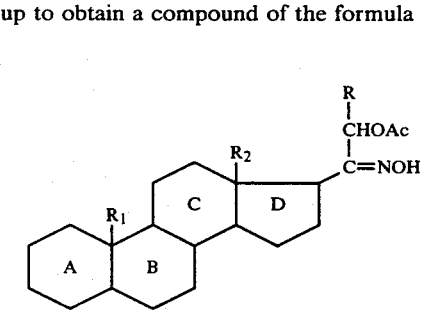

and reacting the latter with a cleavage agent for the oxime group to obtain a compound of the formula

VI'

The reducing agent for the 17(20)-double bond is preferably an alkali metal borohydride such as sodium borohydride but other reducing agents may be used. The other reacting agents preferably used are those indicated in the above process.

In a preferred mode of the invention, 17-(nitromethylene)-Δ$^5$-androstene-3β-ol is reacted with a formylating agent to obtain the compound of the formula

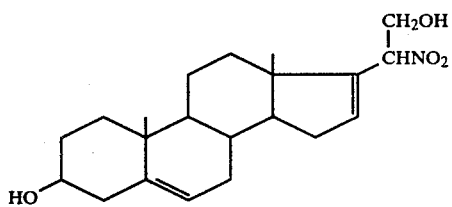

reacting the latter with an acetylation agent to obtain a compound of the formula

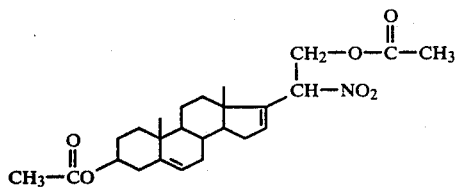

reacting the latter with a reducing agent for nitro to obtain

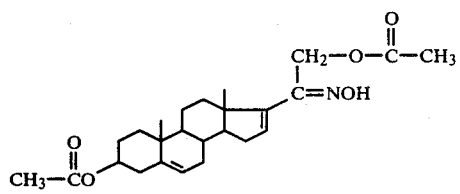

and subjecting the latter to a cleavage agent for oxime functions to obtain

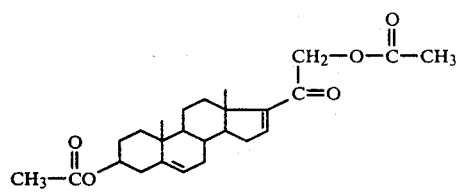

In another mode of the process of the invention, 17-(nitromethylene)-Δ$^5$-androstene-3β-ol is reacted with a reducting agent to obtain a compound of the formula

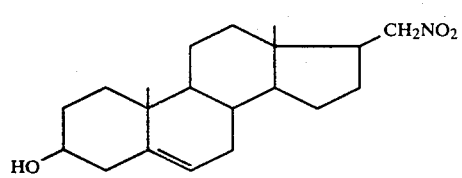

the latter is reacted with a formylation agent to obtain a compound of the formula

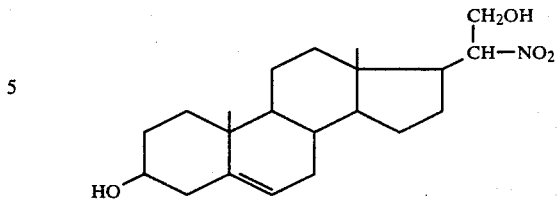

the latter is reacted with an acetylation agent to obtain a compound of the formula

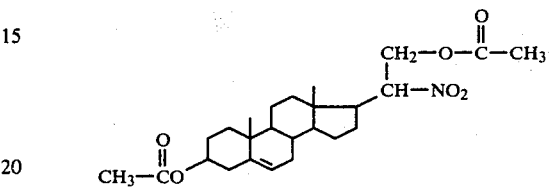

the latter is reacted with a reducing agent for the nitro to obtain a compound of the formula

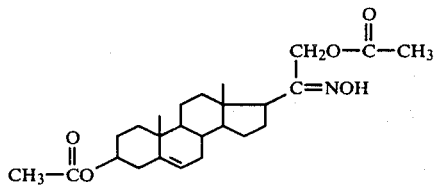

and the latter is reacted with a cleavage agent for the oxime to obtain a compound of the formula

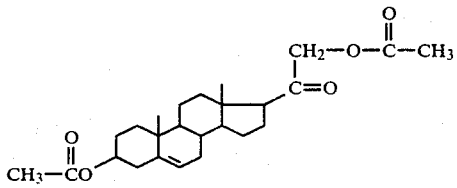

The D homo compounds corresponding to the compounds of formulae VI and VI' are obtained starting with the compounds of formula I. Their obtention is an other object of the invention. The compounds of formulae III, IV, V, VI, VII, III', IV', V' and VI' as well as the corresponding D homo compounds are novel intermediates.

In the following examples there are described several preferred embodiments to illustrate the invention. However, it should be understood that the invention is not intended to be limited to the specific embodiments.

EXAMPLE 1

17-nitromethylene-Δ$^5$-androstene-3β-ol

A solution of 8.7 g of Δ$^5$-androstene-3β-ol-17-one in 150 ml of nitromethane was refluxed under a nitrogen atmosphere while distilling 10 ml of nitromethane and after the addition of 0.1 ml of ethylenediamine, the mixture was refluxed for 50≈60 hours and was evaporated to dryness under reduced pressure. The residue was taken up in dichloromethane and was filtered through silica gel. Elution was effected with a 1-1 ether-dichloromethane mixture and the eluate was evaporated to dryness under reduced pressure to obtain 9.9 g of 17-nitromethylene-Δ⁵-androstene-3β-ol melting at 118°–122° C. The product crystallized with 0.5 mole of methanol melted at 165° to 168° C. and had a specific rotation of $[\alpha]_D^{20} = -88°$ (c=0.76% in methanol).

NMR Spectrum (carbon tetrachloride):
Peaks at 6.65 ppm (1H large 20H); at 5.25 ppm (1H large 6H); at 1.05 ppm (3H singulet 10CH₃); at 0.95 ppm (3H singulet 13CH₃).

EXAMPLE 2

3,4-dihydro-2-nitromethane-naphthalene

A solution of 220 mg of β-tetralone in 3 ml of nitromethane containing 15 mg of ethylenediamine was heated at 75° C. under a nitrogen atmosphere for 18 hours and excess nitromethane was evaporated under reduced pressure. The residue was chromatographed over silica gel and was eluted with a 2-3 benzene-pentane mixture to obtain 232 mg of 3,4-dihydro-2-nitromethane-naphthalene which after crystallization from pentane melted at 29°–31° C. and had an IR spectrum with a max. at 1550 cm⁻¹.

NMR Spectrum (deuterochloroform):
Peaks at 6.9 ppm (4H-aromatic); at 6.4 ppm (1H large singulet ethylenic hydrogen); at 4.9 ppm (2H singulet —CH₂—N₂); at 2.3–3.0 ppm (4H m —CH₂).

Analysis: Calculated: %C 69.96, %H 5.88, %N 7.49, /Found: 69.83, 5.86, 4.40.

EXAMPLE 3

3β,21-diacetoxy-Δ⁵,¹⁶-pregnadiene-20 one

STEP A: 3β,21-diacetoxy-20-nitro-Δ⁵,¹⁶-pregnadiene

A mixture of a suspension of 500 mg of the product of Example 1 in 10 ml of isopropanol and 2 ml of an aqueous formaldehyde solution and 1 ml of triethylamine was stirred at room temperature for 60 minutes and was then poured into aqueous acetic acid. The mixture was stirred for 30 minutes and was filtered. The product was dried to obtain 511 mg of 3β,21-diacetoxy-20-nitro-Δ⁵,¹⁶-pregnadiene melting at 155°–163° C. and having a specific rotation of $[\alpha]_D^{20} = -52°$ (c=0.48% in chloforom).

NMR Spectrum (carbon tetrachloride):
Peaks at 5.95 ppm (1H large 16H); at 5.30 ppm (1H large 6H); 4.9–5.1 ppm (1H large 20OH); at 4.1 to 4.6 ppm (3H large 3H and 21H); at 2.05 ppm and 1.97 ppm (6H singulet acetate); at 1.10 ppm (3H singulet 10—CH₃); at 0.85 ppm (3H singulet 13—CH₃).

STEP B:
3β,21-diacetoxy-20-oximino-Δ⁵,¹⁶-pregnadiene

A solution of 6 ml of concentrated hydrochloric acid and 1.8 g of powdered zinc were added to a solution of 3 g of CrCl₃.6H₂O in 14 ml of water and the resulting solution was filtered. The filtrate was poured into aqueous sodium chloride solution and the mixture was extracted with ether. The organic phase was washed with aqueous sodium chloride and was dried and filtered over silica gel. The filtrate was evaporated to dryness to obtain 830 mg of 3β,21-diacetoxy-20-oximino-Δ⁵,¹⁶-pregnadiene in the form of a white crystalline solid melting at 173°–176° C. and having a specific rotation of $[\alpha]_D^{20} = -42°$ (c=1.06% in CHCl₃).

NMR Spectrum (carbon tetrachloride):
Peaks at 5.97 ppm (1H large 16H); at 5.27 ppm (1H large 6H); at 4.88 ppm (2H singulet 21—CH₂); at 4.3–4.7 ppm (1H large 3H); at 2.04 and 2.00 ppm (6H singulet acetate); at 1.05 ppm (3H singulet 10—CH₃); at 0.94 ppm (3H singulet 13—CH₃).

STEP C: 3β,21-diacetoxy-Δ⁵,¹⁶-pregnadiene-20-one 6.5 ml of an aqueous solution of titanium trichloride were added to a suspension of 800 mg of the product of Step B, 16 ml of acetic acid and 6 ml of acetone containing 2.4 g of ammonium acetate and the mixture was stirred for 6 hours and was poured into water. The mixture was extracted with ether and the organic phase was washed with water, dried and filtered through silica gel. The filtrate was evaporated to dryness to obtain 766 mg of 3β,21-diacetoxy-Δ⁵,¹⁶-pregnadiene-20-one in the form of a white solid melting at 154°–156° C. and having a specific rotation of $[\alpha]_D^{20} = -39°$ (c=0.95% in chloroform).

EXAMPLE 4

3β,21-diacetoxy-Δ⁵-pregnene-20-one

STEP A: 17β-nitromethyl-Δ⁵-androstene-3β-ol 100 mg of sodium borohydride were added in portions over 10 minutes to a suspension of 0.5 g of the product of Example 1 in 15 ml of isopropanol and the mixture was stirred at room temperature for 2 hours and was poured into 300 ml an aqueous 1% acetic acid solution. The mixture was filtered and the product was dried to obtain 0.5 g of 17β-nitromethyl-Δ⁵-androstene-3β-ol melting at 178°–181° C. (methanol) and having a specific rotation of $[\alpha]_D^{20} = -70°$ (c=1% in chloroform) and an IR spectrum with a max. at 1540 cm⁻¹.

NMR Spectrum (deuterochloroform):
Peaks at 5.25 ppm (1H m 6—H); at 4.25 ppm (2H m 20—CH₃); at 3.4 ppm (3H large 3α-H); at 1.05 ppm (3H singulet 19—CH₃); at 0.7 ppm (3H singulet 18—CH₃).

STEP B: 3β,21-diacetoxy-20-nitro-Δ⁵-pregnene 4 ml of formol and 2 ml of triethylamine were added to a suspension of 1 g of the product of Step A in 20 ml of isopropanol and the mixture was stirred at room temperature for 40 to 50 minutes and was poured into 200 ml of aqueous 2.5% acetic acid solution. The mixture was filtered and the product was dried to obtain 1.07 g of 3β,21-diacetoxy-20-nitro-Δ⁵-pregnene melting at 187°–195° C. (methanol) and a specific rotation of $[\alpha]_D^{20} = -22°$ (c=0.4% in chloroform).

STEP C: 3β,21-diacetoxy-Δ⁵-pregnene-20-one

A filtered solution of chromous chloride prepared from 0.6 g of CrCl₃.6H₂O and 0.3 g of zinc powder in solution in 1.5 ml of concentrated hydrochloric acid and 2.5 ml of water was added under nitrogen to a solution of 200 mg of the product of Step B in 35 ml of acetone and after 2 to 3 minutes, the mixture was poured into water. The mixture was extracted with dichloromethane and the organic phase was dried and evaporated to dryness. The residue was dissolved in 4 ml of acetic acid and 2.5 ml of aqueous sodium nitrite and then 4 ml of acetic acid were added thereto dropwise. The mixture was refluxed for 10 minutes and was poured into water. The mixture was neutralized with sodium carbonate and was extracted with dichloromethane. The organic phase was dried, filtered over silica gel and evaporated to dryness to obtain 149 mg of 3β,21-diacetoxy-Δ⁵-pregnene-20-one melting at 162°–164° C. and having a specific rotation of $[\alpha]_D^{20} = +22°$ (c=0.7% in CHCl₃). The melting point was 166°–168° C. and the specific rotation was $[\alpha]_D^{20} = +27°$ as reported by Marquet et al [Bull. Soc. Chim. Fr., 1962, p. 90].

EXAMPLE 5

3-methoxy-17-(nitromethylene)-19-nor-$\Delta^{1,3,5}$-androstatriene

Using the procedure of Example 1, 0.2 g of the methyl ether of estrone, 5 ml of nitromethane and 5 mg of ethylenediamine were reacted to obtain after chromatography over silica gel and elution with a 2-3 hexane-dichloromethane mixture 0.146 g of 3-methoxy-17-(nitromethylene-19-nor-$\Delta^{1,3,5}$-androstatriene melting at 192° to 205° C. and having a specific rotation of $[\alpha]_D^{20} = +10°$ (c=0.78% in chloroform).

EXAMPLE 6

3-nitromethyl-$\Delta^2$-cholestene

A mixture of 0.1 g of cholestanone, 3 ml of nitromethane and 2 mg of ethylenediamine was refluxed for one hour and was evaporated to dryness under reduced pressure to obtain 0.11 g of residue which was crystallized from methanol to obtain 3-nitromethyl-$\Delta^2$-cholestene melting at 108° to 112° C. and having a specific rotation of $[\alpha]_D^{20} = +66°$ (c=0.56% in chloroform).

EXAMPLE 7

2-nitromethylene-adamantane

A mixture of 0.5 g of 2-adamatone, 15 ml of nitromethane and 20 mg of ethylenediamine was refluxed for 3 hours under nitrogen and was evaporated to dryness under reduced pressure at room temperature. The residue was dissolved in methylene chloride and the solution was pass through silica gel and evaporated to dryness to obtain 0.63 g of 2-nitromethylene-adamantane melting at 78° to 81° C.

Various modifications of the products and processes of the invention may be made without departing from the spirit or scope thereof and it is to be understood that the invention is intended to be limited only as defined in the appended claims.

What we claim is:

1. A nitromethylating composition comprising nitromethane and a catalytic amount of a diamine catalyst.

2. The composition of claim 1 wherein the catalyst is selected from the group consisting of ethylenediamine, trimethylenediamine and tetramethylenediamine.

3. In a process for nitromethylating a cyclic or acyclic organic ketone to form the corresponding nitromethylene compound, the improvement comprising using as the nitromethylating composition the composition of claim 1.

4. The process of claim 3 wherein a ketone of the formula

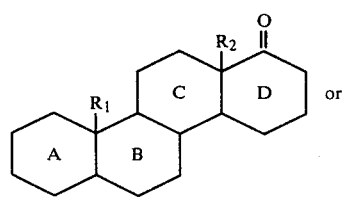

or

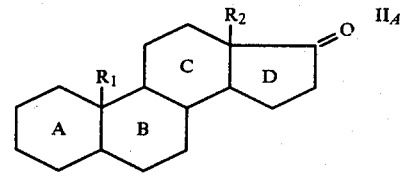

wherein $R_1$ is selected from the group consisting of hydrogen, alkyl of 1 to 4 carbon atoms optionally substituted with an oxygen or nitrogen group or halogen and alkenyl and alkynyl of 2 to 4 carbon atoms, $R_2$ is alkyl of 1 to 4 carbon atoms and the A,B,C, and D rings optionally contain at least one double bond and optionally substituted with at least one member of the group consisting of —OH, =O, halogen, alkyl and alkoxy of 1 to 4 carbon atoms and alkenyl and alkynyl of 2 to 4 carbon atoms is reacted with nitromethane containing a catalytic amount of a bifunctional basic catalyst to obtain a compound of the formula

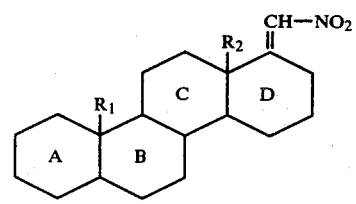

and

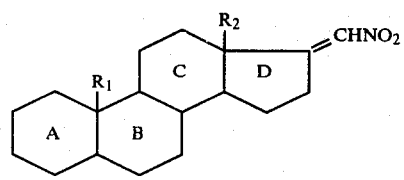

5. The process of claim 4 wherein $R_2$ is methyl and $R_1$ is hydrogen or methyl.

6. The process of claim 5 wherein the starting ketone has the formula

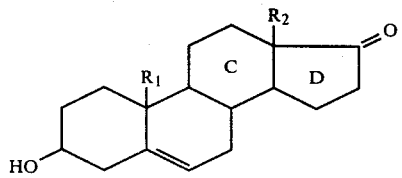

7. The process of claim 6 wherein the starting ketone has the formula

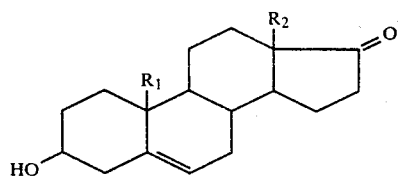

8. The process of claim 7 wherein the starting ketone is $\Delta^5$-androstene-3$\beta$-ol-17-one and the final product is 17-(nitromethylene)-$\Delta^5$-androstene-3$\beta$-ol.

9. A compound selected from the group consisting of steroids of the formula

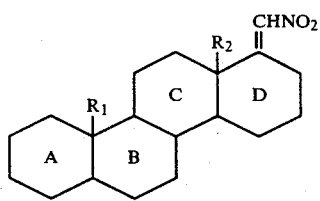

and

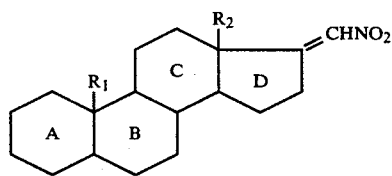

wherein $R_1$ is selected from the group consisting of hydrogen, alkyl of 1 to 4 carbon atoms optionally substituted with an oxygen or nitrogen group or halogen and alkenyl and alkynyl of 2 to 4 carbon atoms, $R_2$ is alkyl of 1 to 4 carbon atoms and the A,B,C and D rings optionally contain at least one double bond and optionally substituted with at least one member of the group consisting of —OH, =O, halogen, alkyl and alkoxy of 1 to 4 carbon atoms and alkenyl and alkynyl of 2 to 4 carbon atoms.

10. A compound of claim 9 which is 17-(nitromethylene)-$\Delta^5$-androstene-3$\beta$-ol.

11. A process for the preparation of a 21-acetoxy -20-keto steroid of the formula

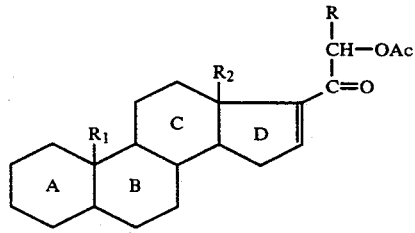

wherein $R_1$ is selected from the group consisting of hydrogen, alkyl of 1 to 4 carbon atoms optionally substituted with an oxygen or nitrogen group or halogen and alkenyl and alkynyl of 2 to 4 carbon atoms, $R_2$ is alkyl of 1 to 4 carbon atoms and the A,B,C and D rings optionally contain at least one double bond and optionally substituted with at least one member of the group consisting of —OH, =O, halogen, alkyl and alkoxy of 1 to 4 carbon atoms and alkenyl and alkynyl of 2 to 4 carbon atoms and R is selected from the group consisting of hydrogen and alkyl of 1 to 18 carbon atoms and Ac is acyl of 1 to 18 carbon atoms comprising reacting a compound of the formula

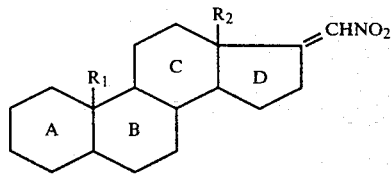

with an aldehyde of the formula RCHO to obtain a compound of the formula

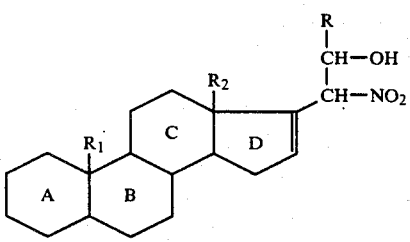

reacting the latter with an esterification agent of an acid of the formula AcOH to obtain a compound of the formula

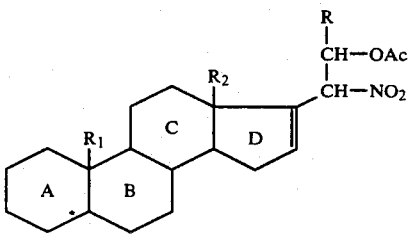

subjecting the latter to a reducing agent for the nitro group to obtain a compound of the formula

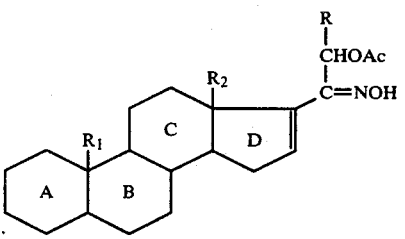

and subjecting the latter to a cleavage agent for the oxime function to obtain a compound of formula VI.

12. A process for the preparation for the preparation of a compound of the formula

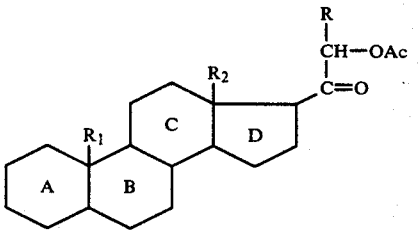

wherein $R_1$ is selected from the group consisting of hydrogen, alkyl of 1 to 4 carbon atoms optionally substituted with an oxygen or nitrogen group or halogen and alkenyl and alkynyl of 2 to 4 carbon atoms, $R_2$ is alkyl of 1 to 4 carbon atoms and the A,B,C and D rings optionally contain at least one double bond and optionally substituted with at least one member of the group consisting of —OH, =O, halogen, alkyl and alkoxy of 1 to 4 carbon atoms and alkenyl and alkynyl of 2 to 4 carbon atoms, R is selected from the group consisting of hydrogen and alkyl of 1 to 18 carbon atoms and Ac is acyl of 1 to 18 carbon atoms comprising reacting a compound of the formula

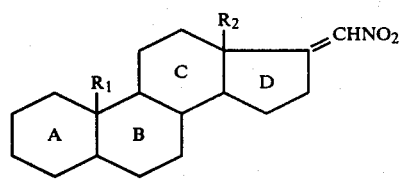

with a reducing agent for the 17(20) double bond to obtain a compound of the formula

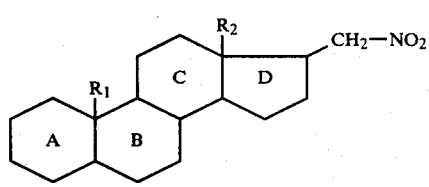      VII reacting the latter with an aldehyde of the formula RCHO to obtain a compound of the formula

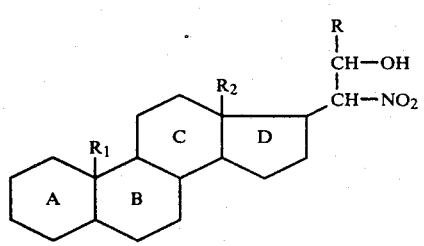      III' reacting the latter with an esterification agent to obtain the compound of the formula

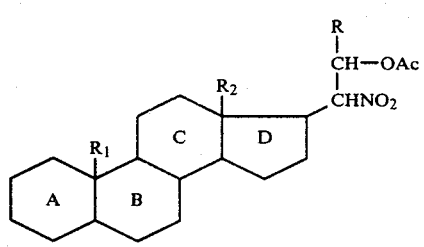      IV' reacting the latter with a reducing agent for the nitro group to obtain a compound of the formula

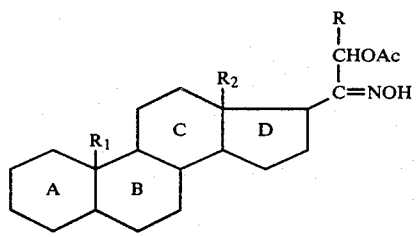      V' and reacting the latter with a cleavage agent for the oxime group to obtain a compound of the formula

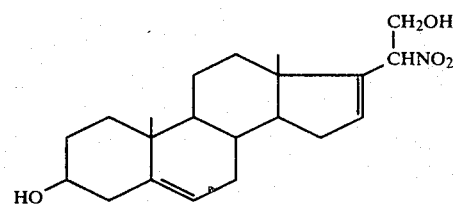      VI'

13. A process comprising reacting 17-(nitromethylene)Δ$^5$-androstene-3β-ol with a formylating agent to obtain a compound of the formula

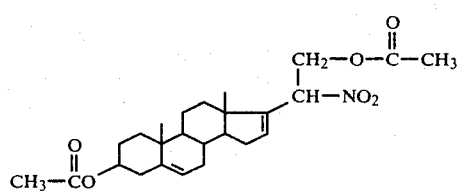

reacting the latter with an acetylation agent to obtain a compound of the formula

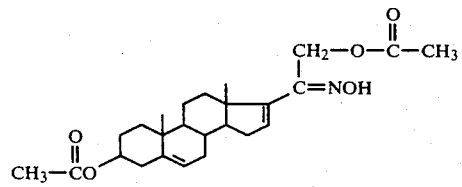

reacting the latter with a reducing agent for nitro to obtain

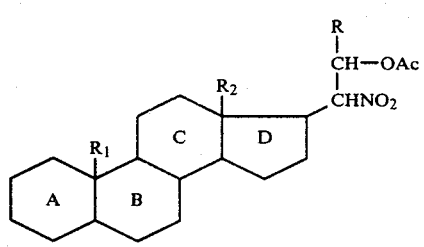

and subjecting the latter to a cleavage agent for oxime function to obtain

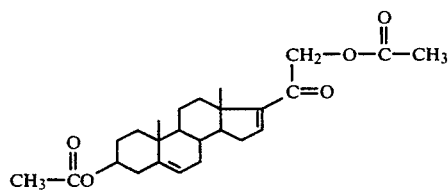

14. A process comprising reacting 17-(nitromethylene)-Δ⁵-androstene-3β-ol with a reducing agent to obtain a compound of the formula

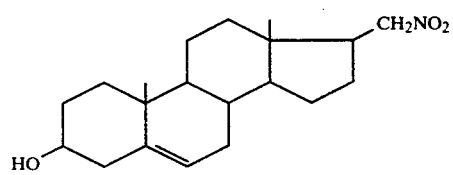

the latter is reacted with a formylation agent to obtain a compound of the formula

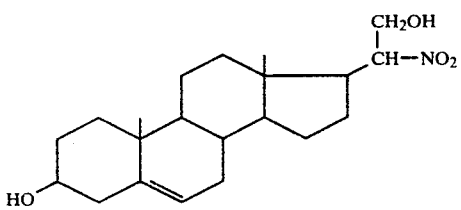

the latter is reacted with an acetylation agent to obtain a compound of the formula

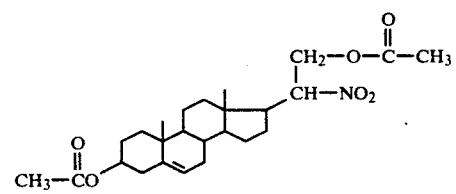

the latter is reacted with a reducing agent for the nitro to obtain a compound of the formula

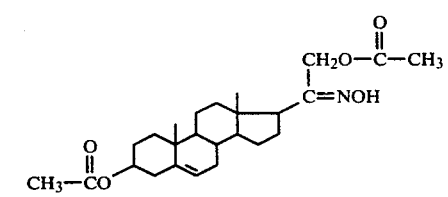

and the latter is reacted with a cleavage agent for the oxime to obtain a compound of the formula

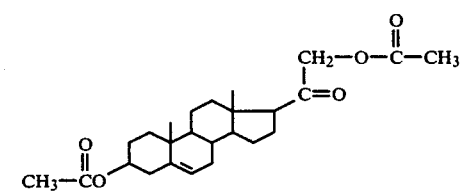

15. A process according to claim 11 for the preparation of D homo compounds corresponding to the compounds of formula VI using as starting compounds, a compound of formula I.

16. A process according to claim 12 for the preparation of D homo compounds corresponding to the compounds of formula VI' using as starting compounds, a compound of formula I.

17. A compound having a formula selected from the group consisting of

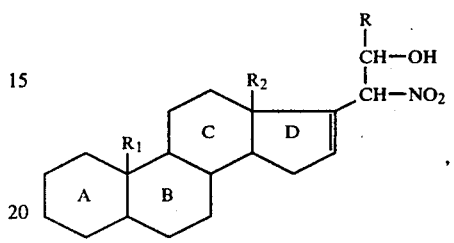

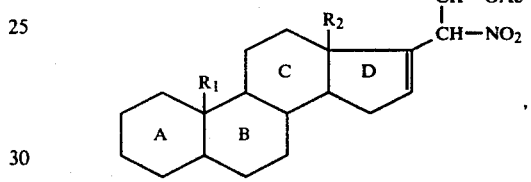

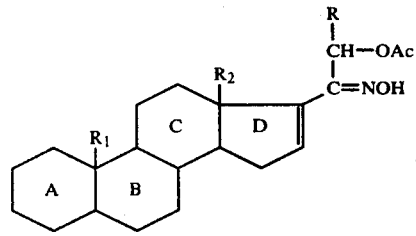

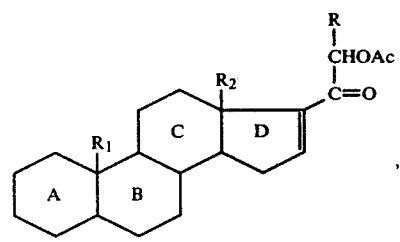

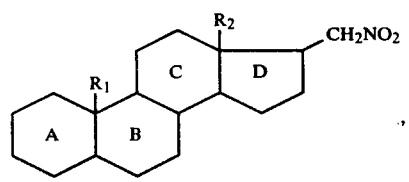

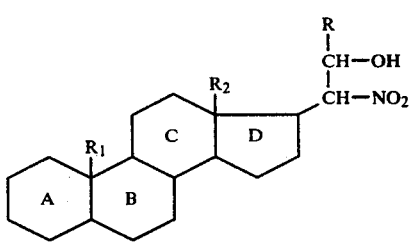

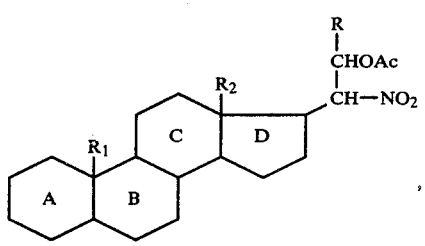

and

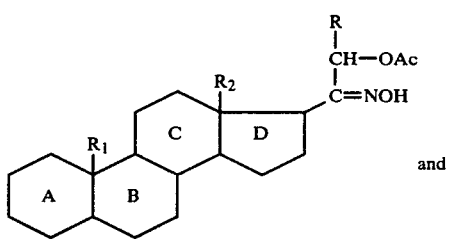

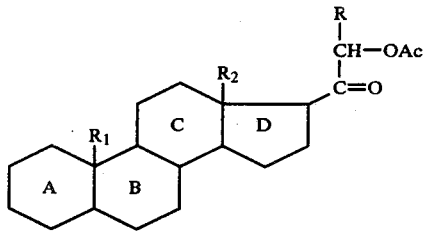

wherein $R_1$ is selected from the group consisting of hydrogen, alkyl of 1 to 4 carbon atoms optionally substituted with an oxygen or nitrogen group or halogen and alkenyl and alkynyl of of 2 to 4 carbon atoms, $R_2$ is alkyl of 1 to 4 carbon atoms and the A,B,C and D rings optionally contain at least one double bond and optionally substituted with at least one member of the group consisting of —OH, =O, halogen, alkyl and alkoxy of 1 to 4 carbon atoms and alkenyl and alkynyl of 2 to 4 carbon atoms, Ac is acyl of 1 to 18 carbon atoms and R is selected from the group consisting of hydrogen and alkyl of 1 to 18 carbon atoms.

* * * * *